(12) United States Patent
Ankarali et al.

(10) Patent No.: US 9,749,086 B1
(45) Date of Patent: Aug. 29, 2017

(54) PHYSICAL LAYER SECURITY FOR WIRELESS IMPLANTABLE MEDICAL DEVICES

(71) Applicants: Zekeriyya Esat Ankarali, Tampa, FL (US); Ali Fatih Demir, Tampa, FL (US); Huseyin Arslan, Tampa, FL (US); Richard Dennis Gitlin, Tampa, FL (US)

(72) Inventors: Zekeriyya Esat Ankarali, Tampa, FL (US); Ali Fatih Demir, Tampa, FL (US); Huseyin Arslan, Tampa, FL (US); Richard Dennis Gitlin, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/198,490

(22) Filed: Jun. 30, 2016

Related U.S. Application Data

(60) Provisional application No. 62/213,866, filed on Sep. 3, 2015.

(51) Int. Cl.
| | |
|---|---|
| *H04K 3/00* | (2006.01) |
| *H04L 5/00* | (2006.01) |
| *H04W 12/08* | (2009.01) |

(52) U.S. Cl.
CPC .............. *H04K 3/84* (2013.01); *H04L 5/0048* (2013.01); *H04W 12/08* (2013.01)

(58) Field of Classification Search
None
See application file for complete search history.

(56) References Cited

U.S. PATENT DOCUMENTS

| | | | |
|---|---|---|---|
| 8,886,316 B1 * | 11/2014 | Juels ................. | A61N 1/37252 607/30 |
| 8,907,782 B2 | 12/2014 | Baker et al. | |
| 2010/0121413 A1 * | 5/2010 | Willerton ............ | A61N 1/3706 607/60 |
| 2010/0198304 A1 * | 8/2010 | Wang ................. | A61N 1/37276 607/60 |
| 2015/0089590 A1 | 3/2015 | Krishnan et al. | |

OTHER PUBLICATIONS

Halperin et al. Pacemakers and implantable cardiac defibrillators: Software radio attacks and zeropower defenses. IEEE Symposium on Security and Privacy. 2008: 129-142.

(Continued)

*Primary Examiner* — Mohammed Rachedine
(74) *Attorney, Agent, or Firm* — Molly L. Sauter; Smith & Hopen, P.A.

(57) ABSTRACT

In various embodiments, the present invention presents a physical layer (PHY) authentication technique for implantable medical devices (IMDs) that does not use existing methods of cryptology. Instead, a friendly jamming mechanism is established and malicious attempts by adversaries are prevented, without sharing any secured information, such as secret keys. In addition to ensuring authentication, the invention also provides advantages in terms of decreasing processing complexity of IMDs and enhances overall communications performance.

18 Claims, 6 Drawing Sheets

(56) References Cited

OTHER PUBLICATIONS

Malasri and Wang. Securing wireless implantable devices for healthcare: Ideas and challenges. IEEE Comm. Mag. 2009. vol. 47: 74-80.

Maisel and Tadayoshi. Improving the security and privacy of implantable medical devices. New England journal of medicine. 2010. vol. 362 (No. 13): 1164-1166.

Zhang et al. Physical layer security for two way relay communications with friendly jammers. IEEE Global Telecommunications Conference (GLOBECOM 2010). 2010: 1-6.

Fu. Inside risks: Reducing risks of implantable medical devices. Communications of the ACM. 2009. vol. 52 (No. 6): 25-27.

Ankarali et al., A comparative review on the wireless implantable medical devices privacy and security. 2014 EAI 4th International Conference on Wireless Mobile Communication and Healthcare (Mobihealth). 2014: 246-249.

Gollakota et al., They can hear your heartbeats: non-invasive security for implantable medical devices. ACM SIGCOMM Computer Communication Review. 2011. vol. 41: 2-13.

Demir et al., Numerical characterization of in vivo wireless communication channels. 2014 IEEE MTT-S International Microwave Workshop Series on RF and Wireless Technologies for Biomedical and Healthcare Applications (IMWS-Bio). 2014: 1-3.

Javali et al. SeAK: Secure Authentication and Key Generation Protocol Based on Dual Antennas for Wireless Body Area Networks. Lecture Notes in Computer Science, Chapter: Radio Frequency Identification: Security and Privacy Issues. 2014. vol. 8651: 74-89.

Al-Hassanieh. Encryption on the air: non-invasive security for implantable medical devices. Diss. Massachusetts Institute of Technology. 2011: 1-78.

Shi et al. Bana: body area network authentication exploiting channel characteristics. IEEE Journal on Selected Areas in Communications. 2013. vol. 31 (No. 9): 1803-1816.

Allouche et al. Secure Communication through Jammers Jointly Optimized in Geography and Time. 2015: 1-11.

\* cited by examiner

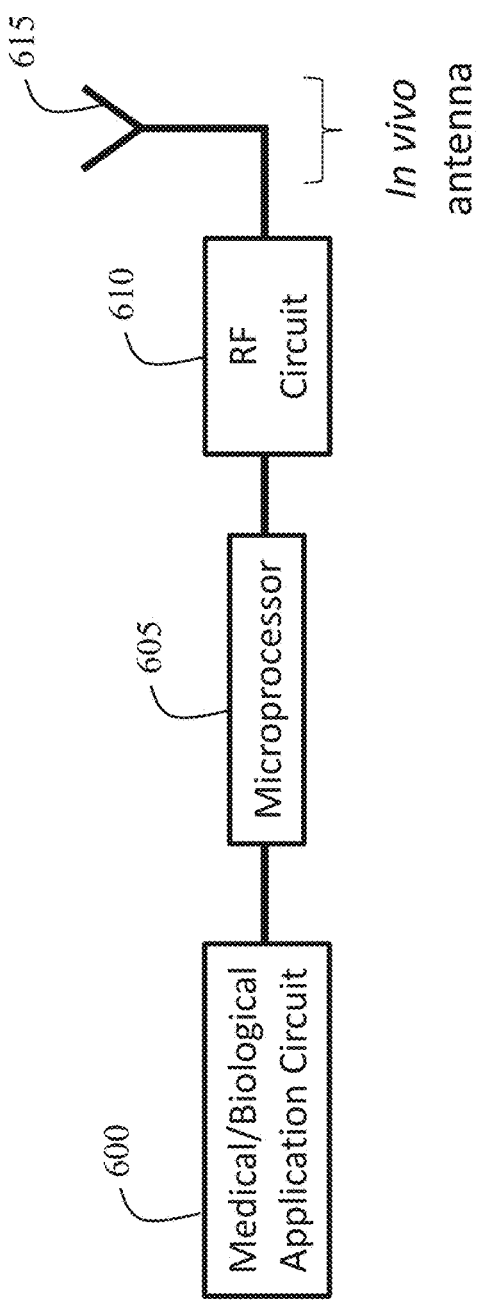
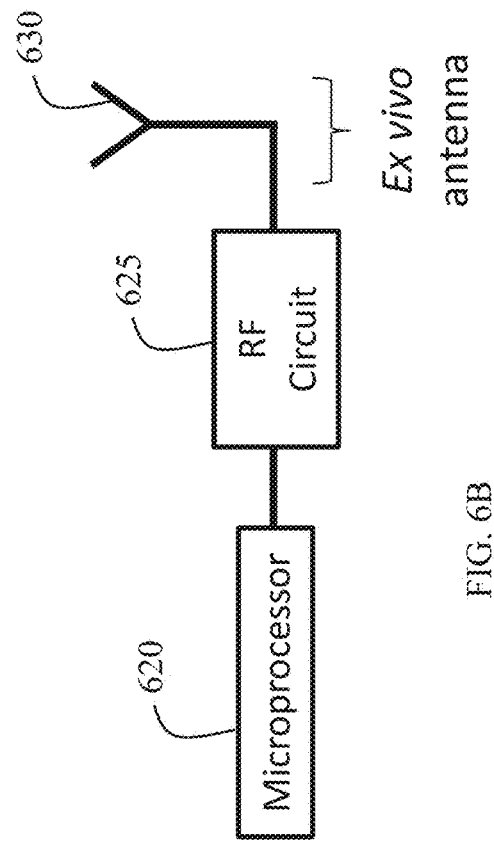
FIG. 6A
FIG. 6B

PHYSICAL LAYER SECURITY FOR WIRELESS IMPLANTABLE MEDICAL DEVICES

CROSS-REFERENCE TO RELATED APPLICATIONS

This application claims priority to currently U.S. Provisional Patent Application 62/213,866 entitled, "Physical Layer Security for Wireless Implantable Medical Devices", filed Sep. 3, 2015.

BACKGROUND OF THE INVENTION

Wireless communications are increasingly important in health-care applications, particularly in those that use implantable medical devices (IMDs). Such systems have many advantages in providing remote healthcare in terms of monitoring, treatment, and prediction of critical cases. However, the existence of malicious adversaries, referred to as Adversaries (ADs), which attempt to externally control implanted devices, present a critical risk to patients. Such adversaries may perform dangerous attacks by sending malicious commands to the IMD and any weakness in the device authentication mechanism may result in serious problems, including death.

Accordingly, what is needed in the art is an improved authentication system and method for the prevention of dangerous adversarial attacks on implantable medical devices.

SUMMARY OF INVENTION

In various embodiments, the present invention presents a physical layer (PHY) authentication technique for implantable medical devices (IMDs) that does not use existing methods of cryptology. Instead, a friendly jamming based mechanism is established and malicious attempts by adversaries are prevented, without sharing any secured information, such as secret keys. In addition to ensuring authentication, the invention also provides advantages in terms of decreasing processing complexity of IMDs and enhances overall communications performance.

The present invention includes a novel authentication mechanism between a wireless implantable medical devices (IMD) and a wearable external devices (WED). The authentication mechanism of the present invention prevents adversaries from controlling the IMD through the wireless channel.

In one embodiment, a method for preventing unauthorized wireless communication with an implantable medical device is provided. The method includes, receiving a pilot signal request at an implantable medical device over a wireless channel and transmitting a pilot signal from the implantable medical device over the wireless channel in response to receiving the pilot signal request. The method further includes receiving the pilot signal at a wearable external device and estimating the wireless channel, at the wearable external device, using the received pilot signal, pre-equalizing one or more command signals based upon the estimation of the wireless channel to generate one or more pre-equalized command signals, transmitting the pre-equalized command signals from the wearable external device over the wireless channel and receiving the pre-equalized command signals at the implantable medical device. In this embodiment, the pilot signal request is transmitted from the wearable external device over the wireless channel and it is assumed that a distance between the adversary device and the implantable medical device is greater than a distance between the wearable external device and the implantable medical device, such that the channel estimation of adversary device is more noisy than the channel estimation of the wearable external device.

In addition, when the channel estimation of the adversary device is not more erroneous than the channel estimation of the wearable external device because the adversary device is not far away from the implantable medical device or equipped with advanced hardware, a friendly jamming algorithm is proposed to secure access to the implantable medical device. In accordance with this additional embodiment, wherein the pilot signal request is transmitted from an adversary device over the wireless channel, the method further includes, receiving the pilot signal at the wearable external device and determining at the wearable external device that the wearable external device did not transmit the pilot signal request and transmitting a jamming signal over the wireless channel to prevent the implantable medical device from receiving any signals transmitted from the adversary device over the wireless channel.

In a specific embodiment, the method may further include applying a blocking mechanism at the implantable medical device to prevent the implantable medical device from receiving any signals transmitted over the wireless channel. In this embodiment, the implantable medical device applies a blocking mechanism based upon a predetermined power threshold and the implantable medical device stops taking action if a received signal power is greater than the predetermined power threshold. In this way, the implantable medical device prevents an adversary device from utilizing a high power signal to dominate the jamming signal.

The implantable medical device may be selected from the group consisting of pacemakers, implantable cardiac defibrillators (ICDs), drug delivery systems and neurostimulators. This list is not intended to be limiting and other implantable medical devices are considered within the scope of the present invention.

In an additional embodiment, the present invention provides a system which includes, an implantable medical device comprising circuitry for receiving a pilot signal request over a wireless channel and for transmitting a pilot signal over the wireless channel in response to receiving the pilot signal request and a wearable external device comprising circuitry for receiving the pilot signal, for estimating the wireless channel using the received pilot signal, for pre-equalizing one or more command signals based upon the estimation of the wireless channel to generate one or more pre-equalized command signals, and for transmitting the pre-equalized command signals from the wearable external device over the wireless channel. The wearable external device may further include circuitry for transmitting the pilot signal request from the wearable external device over the wireless channel.

In a particular embodiment, wherein the pilot signal request is transmitted from an adversary device over the wireless channel, the wearable external device may further include circuitry for receiving the pilot signal, for determining that the wearable external device did not transmit the pilot signal request and for transmitting a jamming signal over the wireless channel to prevent the implantable medical device from receiving any signals transmitted from the adversary device over the wireless channel.

In a specific embodiment, the implantable medical device may further include circuitry for applying a blocking mechanism to prevent the implantable medical device from receiving any signals transmitted over the wireless channel. In this embodiment, the implantable medical device applies a blocking mechanism based upon a predetermined power threshold and the implantable medical device stops taking action if a received signal power is greater than the predetermined power threshold. In this way, the implantable medical device prevents an adversary device from utilizing a high power signal to dominate the jamming signal.

As such, the present invention provides an improved system and method for the prevention of dangerous attacks on implantable medical devices that was not previously known or anticipated in the prior art.

BRIEF DESCRIPTION OF THE DRAWINGS

For a fuller understanding of the invention, reference should be made to the following detailed description, taken in connection with the accompanying drawings, in which:

FIG. 6A is a block diagram illustrating an implantable medical device, in accordance with an embodiment of the present invention.

FIG. 6B is a block diagram illustrating a wearable external device, in accordance with an embodiment of the present invention.

DETAILED DESCRIPTION OF THE PREFERRED EMBODIMENT

Figure 1:
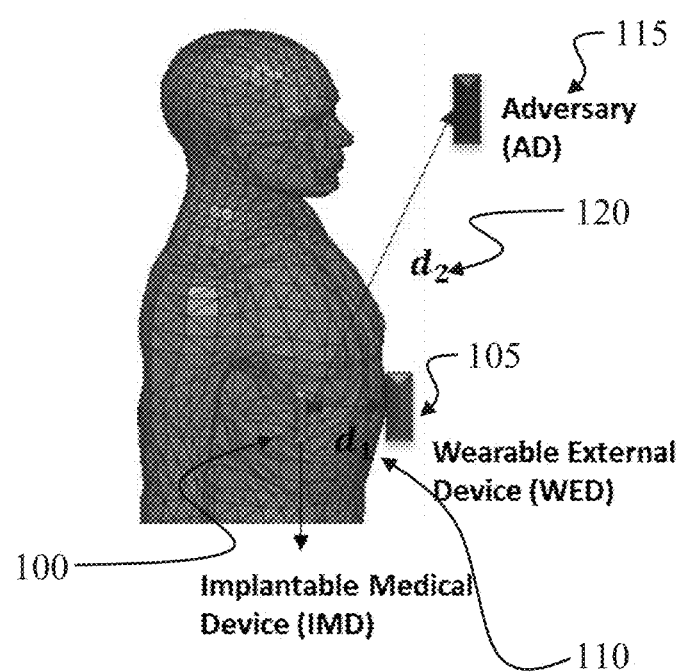
FIG. 1 is an illustration of the system scenario where an adversary or adversaries may compromise the safety of a patient utilizing an implantable medical device (IMD), in accordance with an embodiment of the present invention.

Implantable medical devices (IMDs), such as pacemakers, implantable cardiac defibrillators (ICDs), drug delivery systems and neurostimulators, have a vital importance in the medical field. These devices provide a substantial advantage by enabling physicians to manage many diseases by providing for the identification, monitoring, and treatment of patients anywhere, at anytime, thereby saving innumerable lives. Such IMDs have already been deployed in many patients and their usage is expected to expand in the near future. For example, the number of insulin pump users in 2005 was about 245,000, and the expected growth rate for the insulin pump market is estimated at approximately 9% between 2009 and 2016.

While many IMDs are able to perform complex analyses and sophisticated decision-making algorithms, in addition to storing detailed personal medical data, wireless signals transmitted by the IMD which convey critical information, require protection from a variety of attacks. The IMD may include circuitry such as a wireless transceiver, signal processor, central processing unit and memory. Considering the growing utilization of IMDs and their associated security risks, comprehensive techniques are required to ensure that the patients can use IMDs confidently and without harm.

Authentication is a critical security measure, since an adversary may wirelessly change various parameters of the IMD, which may place the patient in danger. For example, an insulin pump user may face an overdose attack that may even result in death. In the current state of the art, proposed protection techniques against such attacks can be classified into three main categories, cryptography, anomaly detection and "friendly" jamming.

Cryptography relies on a secret key shared between the IMD and the wearable external device (WED). However, cryptography may not be properly deployed if the limitations of IMDs are considered. For example, cryptography based techniques conflict with the accessibility requirement of IMDs in the case of any emergency, since the closest physician may not have the secret key. As such, the physician may not be able to perform urgent modifications to the IMD parameters and the patient may experience serious medical problems.

Anomaly detection techniques rely on the ability of the IMD to determine the legitimacy of received commands based on the variance of IMD parameter values that are observed over time. However, such a mechanism does not adapt to new conditions of the patient, as it requires long-term monitoring and data analysis to achieve a reasonable performance.

The friendly jamming technique attempts to sense the existence of a malicious attack and prevents the reception of illegitimate commands by jamming the IMD with the help of an external device. Although, it does not have a direct conflict with IMD requirements, the reduction in the energy efficiency of the wearable external device is a drawback as the wearable external device is required to perform complex and power consuming operations, such as continuous spectrum sensing and jamming, which may preclude normal IMD operation.

In the present invention, a wearable external device (WED) is attached to the body of the patient. The WED may include circuitry such as a wireless transceiver, signal processor, central processing unit and memory. The WED acts as a relay between the IMD and a central external node, and provides a substantial advantage in terms of reducing the IMD's energy consumption for signal transmission and processing. Considering the daily life of patients using an IMD, device size should generally be as small as possible to allow for maximum comfort. However, the reduced size of the IMD may limit the quality of the hardware components of the device. On the other hand, such is not the case for wearable external devices (WEDs), as they are located external to the body of the patient. As such, more advanced and powerful components can be deployed in the WED associated with the IMD.

The present invention proposes a system and method for a pre-equalization based wireless communication system between the IMD and the WED. The present invention improves the performance of the IMD by offloading channel estimation to the WED, thereby decreasing the processing requirements of the IMD and most importantly, by providing reliable authentication at the physical layer.

An illustration of an embodiment of the present invention is shown with reference to FIG. 1. Considering the small distance ($d_1$) 110 between the implantable medical device (IMD) 100 and the wearable external device (WED) 105, the resulting path loss is lower than that experienced by an adversary (AD) node 115 that is located relatively far away (d$_2$) 120 from the patient 125. As such, nodes that are more distant that the WED 105 from the IMD 100 may be considered to be adversaries 115. The objective of the present invention is to prevent any adversary (AD) 115 from controlling the IMD 100.

In order to prevent an adversary 115 from the controlling the IMD 100, in the present invention, in response to a pilot transmission request transmitted from the WED 105, the IMD 100 transmits one or more pilot signals. The pilot signals are received by the AD 115 and the WED 105. The pilot signals from the IMD 100 enable the AD 115 and the WED 105 to estimate the wireless communication channel between the devices. The channel estimation performed by the AD 115 and the WED 105 identify the characteristics of the wireless channel used to transmit the pilot signal. Using its channel estimation, the WED 105 then pre-equalizes a wireless control signal. Pre-equalizing the control signal may include reducing the amplitude, frequency and phase distortion of the channel based upon the channel estimation, with the intent of improving transmission performance. The basic operation of channel estimation and pre-equalization of the control signal is to reverse the effect of the wireless channel. The pre-equalized control signal is then transmitted back to the IMD 100. The AD 115 may also use its channel estimation to pre-equalize a wireless data signal that is transmitted back to the IMD 100. Assuming that an AD 115 cannot be closer to the IMD 100 than the WED 105, the pilot signals from the IMD 100 will be received at the adversary 115 with much less power and with greater dispersion than the pilot signals received at the WED 105, thereby causing the AD 115 to erroneously estimate the wireless channel. Pre-equalization of the wireless data signal utilizing erroneous channel estimation leads to a significant distortion in the AD's wireless data signal transmitted to the IMD 100. As such, an attempt by an adversary 115 to communicate with the IMD 100 will fail, even if the transmitted signal is extremely powerful. In this way, adversaries 115 trying to control or mislead IMDs 100, from relatively distant locations, can be prevented from achieving impersonation attacks on the IMD 100.

However, these aforementioned techniques may not ensure security if the adversary 115 utilizes a highly advanced signal processing algorithm to estimate the channel or includes hardware having a very small noise floor. Under these conditions, the adversary 115 may still be able to properly estimate the channel from the pilot signals provided by the IMD 100. In the case of such a scenario, the present invention may additionally include a "friendly jamming" mechanism. In order to achieve this, the pilot signal is designed to be transmitted by the IMD 100 as a "wake-up" signal for the WED 105. If the pilot signal is transmitted upon the request for a pilot signal transmission from an unauthorized user, such as an adversary 115, the WED 105 recognizes that the IMD 100 is transmitting pilot signals even though a request for a pilot signal from the IMD 100 has not be requested by the WED 105. In response, the WED 105 sends a jamming signal to the IMD 100 that prevents the circuitry of the IMD 100 from decoding any received data signals. This capability is extremely important for the IMD 100 to retain the ability to continue to treat the patient while also resisting the AD 115 attack, because any miss treatment, e.g., high voltage injection for a pacemaker or overdosing of an insulin pump, may result in serious harm to the patient, possibly including death.

In addition, since equalization is performed by the WED 105, instead of the IMD 100, the proposed technique provides for a power efficient processing of the wireless signals. More advanced components can be deployed in the WED 105 because of its size flexibility, as compared to the IMD 100, accordingly, channel estimation performance can be considerably enhanced. Channel estimation performed by a WED 105 can be much better than that performed by an IMD 100 as a result of the increased capabilities of the wearable external device 105. For example, more advanced device components exhibiting a lower noise floor can be used in the design of WED 105, thereby reducing the channel estimation error. As a result, pre-equalization performed by the WED 105 improves the communication between the WED 105 and the IMD 100.

As illustrated in FIG. 1, wireless ADs 115 may perform various malicious attacks which compromise the safety of an IMD 100. In accordance with the present invention, in response to a pilot transmission request from the WED 105, the IMD 100 transmits a pilot signal, p(t), that is used to enable the WED 105 to estimate the wireless channel. Then channel estimation is performed as $$h_\epsilon(t) = h(t) + w(t)p^{-1}(t), \quad (1)$$

where w(t) is the additive noise. Note that $h_\epsilon$, is defined as a scalar value, i.e., a one-tap channel estimation is performed for pre-equalization considering the non-dispersive medium between the IMD 100 and the wearable external device (WED) 105. Then, the analytical expression of the baseband signal transmitted from WED can be given as $$s(t) = h_\epsilon^{-1} \sum_{n=-\infty}^{\infty} X_n g(t - n\tau_0), \quad (2)$$

where n, g(t) and $\tau_0$ indicate the index of QAM symbol, pulse shaping filter and time spacing between the symbols, respectively. After passing through the linear time-variant channel, h(t), the received signal, including the additive noise, can be written as $$y(t) = \int_{-\infty}^{\infty} h(\tau)x(t-\tau)d\tau \quad (3)$$

Assuming the channel is a one-tap channel, due to the small distance between communicating nodes, the received signal can be shown as $$r(t) = h(t)x(t) + w(t), \quad (4)$$

where h(t) denotes the channel gain as a function of time, and w(t) is the additive noise.

In channel estimation, received pilot symbols are also subject to the channel impairments. Therefore, the estimated channel response can be given as $$\hat{h} = h + \underline{w(t)/P}_\epsilon, \quad (5)$$

where P indicates the pilot symbol and E stands for the error in channel estimation. Its effect on bit-error-rate (BER) performance should be investigated to identify the secure region around the patient's body.

Considering more sophisticated attacks where ADs 115 are equipped with highly advanced devices, an additional mechanism is proposed to ensure authentication. Here, the pilot signal sent by the IMD 100 is regarded as a "wake-up" message for the WED 105. If an AD 115 requests a pilot signal transmission from the IMD 100, to establish a communication path prior to sending an unauthorized command to the IMD 100, the WED 105 activates as soon as the IMD 100 sends the pilot signal. Since the WED 105 can easily understand that an unauthorized user made the request for the pilot signal transmission from the IMD 100, the WED 105 sends a jamming signal and blocks all signal reception by the IMD 100. Additionally, it is possible that a powerful AD 115 may send its commands to the IMD 100 at the same time as the WED 105 and the data signal from the AD 115 may dominate the WED's 105 jamming signal utilizing a very high power signal. In order to overcome this issue, the IMD 100 may implement a power threshold criteria that does not allow the circuitry of the IMD 100 to decode a received message that exceeds a predetermined power level. If the WED 105 transmits the jamming signal close to the power level threshold of the IMD 100, additional AD 115 signals will likely exceed the pre-determined power threshold and the IMD's 100 reception of the AD 115 signals will be blocked. In this way, the AD will be disabled from maliciously controlling the IMD.

The major effect of a narrow band wireless signal is path loss for in-body communications, as dispersion in time is generally small compared to the data symbol duration. Also, considering a stationary environment, the frequency dispersion effect of the channel may not need to be taken into account. Note that accounting for dispersion gives more degrees of freedom to provide security. Therefore, the one-tap technique may be viewed as a worst case scenario. In order to investigate the channel effect on legitimate and malicious nodes, a path loss channel model obtained as the function of distance for a body centric communication environment should be used. The general expression for such a model is given as $$P_{dB} = P_{0dB} + 10n\log\left(\frac{d}{d_0}\right) \quad (6)$$

where d is the distance, do is the reference distance and $P_{0dB}$ is the path loss for reference distance. Parameters for an exemplary body model are shown in the Table 1.

TABLE I

PATH-LOSS MODEL PARAMETERS

| Parameters | Parameter Value |
|---|---|
| n | 7.2 |
| $d_0$ | 0.1 m |
| $P_{0dB}$ | 50.5 dB |

In order to investigate the performance of the users located far away from each other, different channel models may be superposed with the given model. However, in this exemplary embodiment, only the users nearby the patient have been considered. Therefore, only the given model of the exemplary embodiment will be taken into account in the numerical results.

Performance of the proposed technique is presented using MATLAB simulations. The effect of the distance between the IMD 100 and other devices on the BER performance is investigated. As previously mentioned, a greater distance between the IMD 100 and the other devices corresponds to a larger path loss. As a device is moving away from the IMD 100, the power of the received pilot signal becomes weaker, which will result in an error in the channel estimation. As shown with reference to FIG. 1, a command signal that is pre-equalized with erroneous channel estimation resulting from the week pilot signal will naturally cause a distortion in the signal, independent of the signal's SNR.

Figure 2:
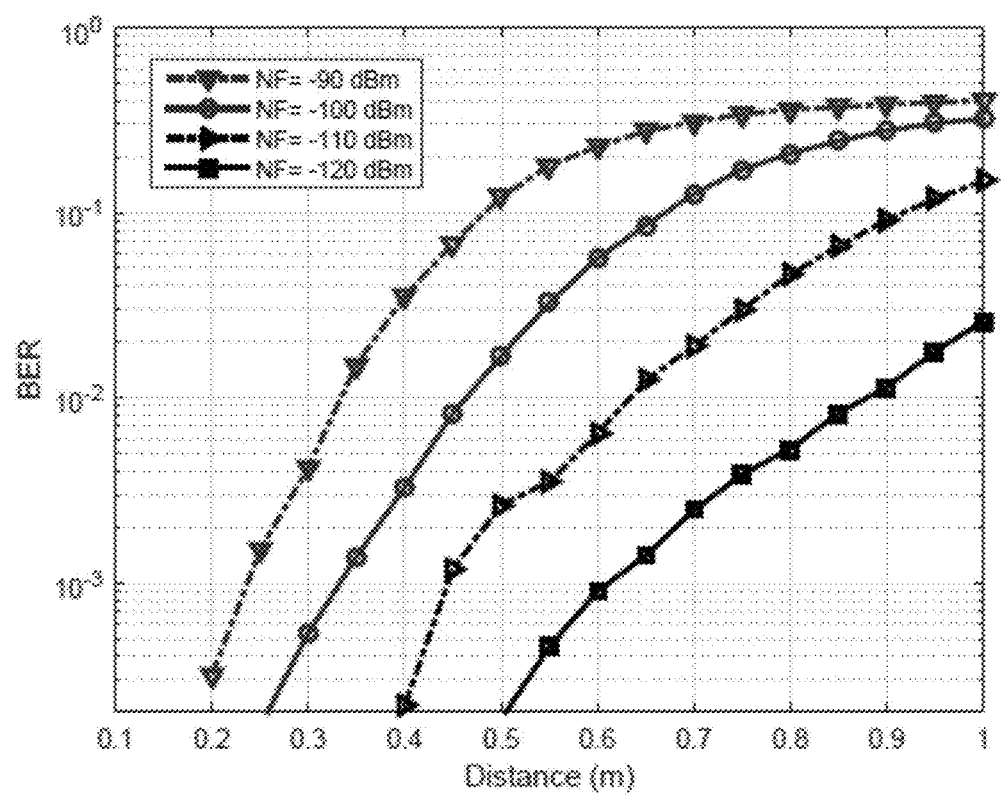
FIG. 2 is a graphical illustration of bit error ratio (BER) performance vs. distance for different noise floors (NFs) affecting the channel estimation performance of the wearable external device (WED) or an adversary in accordance with an embodiment of the present invention.

FIG. 2 illustrates the BER results of a command signal that is sent from different distances, where the SNR of the received signal is specified as 100 dB in order to see the effect of channel estimation error only. As shown in FIG. 2, increasing the distance between the AD 115 and the IMD 100 results in an increased channel estimation error, which dramatically degrades the BER performance. For example, if an adversary 115 is located 90 cm away from the IMD 100, more than 1% error probability is experienced for a signal with 0 dBm transmission power and −120 dBm noise floor (NF) at the AD 115.

Considering the scenario where the AD 115 is capable of performing strong signal processing and utilizes more advanced hardware having a very low noise floor, the self-jamming approach is deployed to ensure authentication with the IMD 100.

Figure 3:
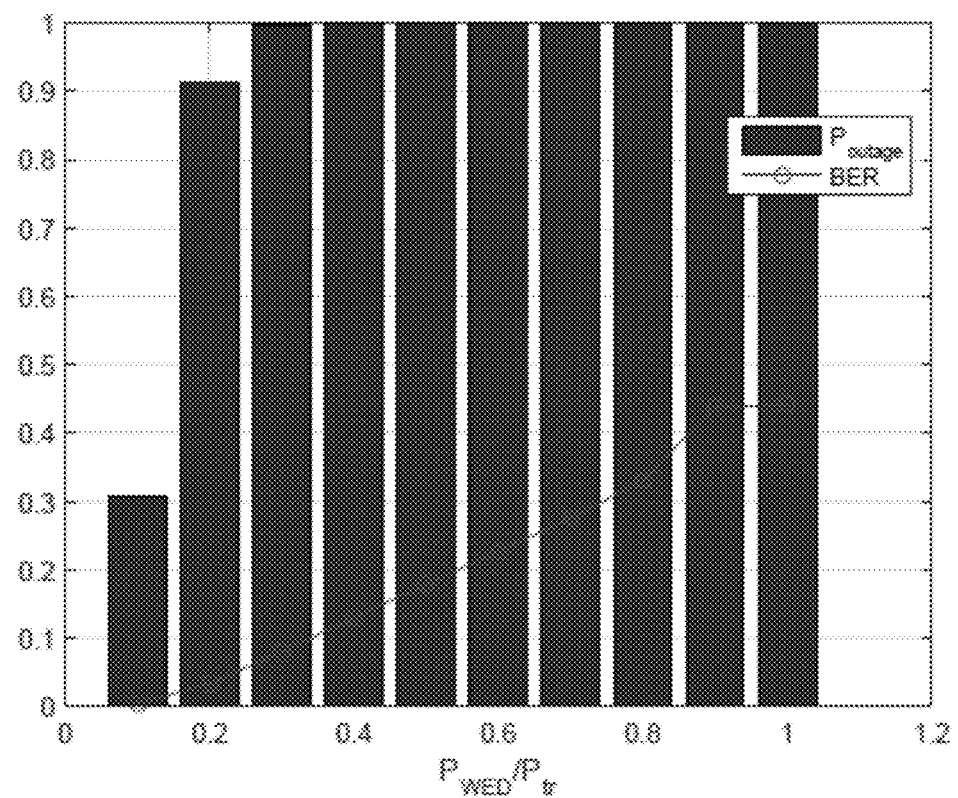
FIG. 3 is graphical illustration of the adversary outage probabilities for different jammer signal powers in terms of the threshold power ($P_{tr}$), in accordance with an embodiment of the present invention.

In addition, as previously discussed, the IMD 100 may apply a power-limitation criterion in order to prevent the AD 115 from dominating the WED's 105 jamming signal. While determining the WED's 105 jamming signal power, $P_{WED}$, a power threshold $P_{tr}$ is used as a metric, i.e., $P_{WED}$ is specified in terms of Pr. Command signals are designed as packets consisting of 150 QPSK symbols and the outage probability of these packets will be used as the performance measure. In FIG. 3, outage probabilities for different jamming powers indicated as $P_{WED}/P_{tr}$ are given for the AD 115 along with the bit-error probabilities. In this exemplary embodiment, it is assumed that the AD 115 has perfect channel estimation and its signal has a 20 dB SNR. Even in such an extreme case, the AD's 115 packets are all distorted when $P_{WED}$ is 30% of $P_{tr}$. As such, the command signal from the AD 115 will be blocked once the $P_{WED}/P_{tr}$ exceeds 0.3 and proper authentication between the IMD 100 and the WED 105 can be ensured.

Figure 4:
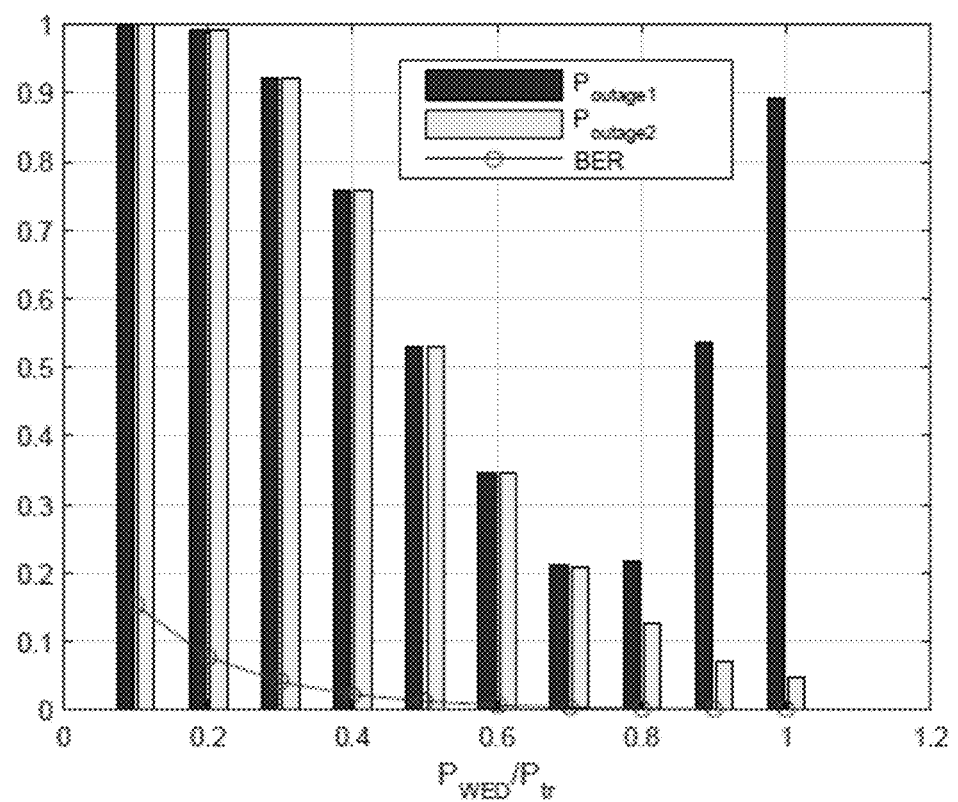
FIG. 4 is graphical illustration of the outage probabilities of WED command with and without proposed technique represented by $P_{outage1}$ and $P_{outage2}$, respectively, in accordance with an embodiment of the present invention.

The effect of the proposed technique on the desired communication signals between the IMD 100 and the WED 105 is also investigated. The power of the WED's 105 signal is very critical since the IMD 100 may halt reception of the WED's 105 signal based upon the power level of the received signal. If the WED's 105 signal power exceeds $P_{tr}$ after being combined with noise, legitimate commands may be eliminated as well. In FIG. 4, outage probabilities are given as $P_{outage1}$ and $P_{outage2}$ for the WED's 105 command with and without the proposed technique of the present invention, respectively. For small power values, outage probability for both cases is almost equal to each other. Here, $P_{WED}$ is given as 0 dBm and if the $P_{WED}/P_{tr}$ ratio is 1, the SNR of the received signal is specified as 20 dB, i.e., noise floor of the IMD 100 is adjusted for 20 dB SNR. Then, if $P_{WED}/P_{tr}$ ratio is 0.1, the SNR becomes 10 dB and the outage probability approaches unity. The proposed technique does not degrade the successful transmission performance of the WED 105 unless $P_{WED}/P_{tr}$ is greater than 0.7. After that level, the probability of blocking the WED's 105 packets increases because its signal transmission power is approaching the threshold. Therefore, jamming power of WED 105, $P_{WED}$, should be carefully selected by considering the WED's 105 performance and authentication requirements.

Figure 5:
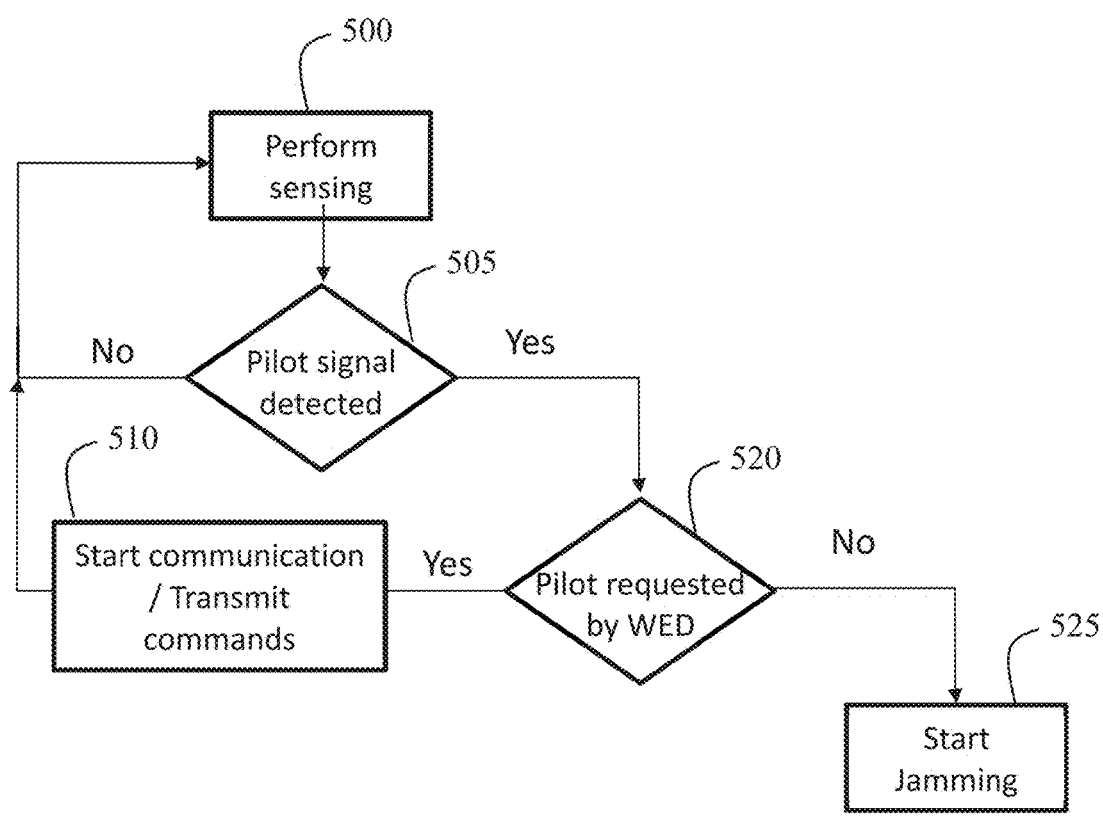
FIG. 5 is a flow diagram illustrating a method for securing access to an implantable medical device, in accordance with an embodiment of the present invention.

With reference to FIG. 5, a flow diagram illustrates an embodiment of the method of the present invention, which includes, the WED performing sensing 500 for a pilot signal from the IMD. The WED continuously senses for the pilot from the IMD and if a pilot signal is detected 505, the WED may determine whether or not the WED requested the pilot signal from the IMD 520. If the WED did request the pilot signal from the ID, then the method continues by initiating communication between the WED and the IMD 510. However, if it determined that the WED did not request the pilot signal from the IMD, the WED then proceeds to transmit a jamming signal 525 to prevent an AD from accessing the IMD.

In order to perform the secure access method of the present invention, the IMD and the WED may include specific hardware elements. With reference to FIG. 6A, the IMD includes circuitry for receiving a pilot signal request over a wireless channel and for transmitting a pilot signal over the wireless channel in response to receiving the pilot signal request. As such, the circuitry of the IMD may include, a medical/biological application circuit 600, a microprocessor 605 coupled to the medical/biological application circuit 610, an RF circuit 615 coupled to the microprocessor 605 and an in vivo antenna 615 coupled to the RF circuit 615. With reference to FIG. 6B, the WED includes circuitry for receiving the pilot signal, for estimating the wireless channel using the received pilot signal, for pre-equalizing one or more command signals based upon the estimation of the wireless channel to generate one or more pre-equalized command signals, and for transmitting the pre-equalized command signals from the wearable external device over the wireless channel. As such, the circuitry of the WED may include, a microprocessor 620, an RF circuit 625 coupled to the microprocessor and an ex vivo antenna 630 coupled to the RF circuit 625.

In accordance with the present invention, a physical layer authentication technique based on pre-equalization is proposed for implantable medical devices. In addition to providing authentication, the technique of the present invention can also enhance channel estimation performance by utilizing more advanced hardware and signal processing complexity in the WED because of its location external to the patient, wherein the WED is not limited in size, as are the IMDs. While the exemplary embodiment only considered path loss for the in vivo channel estimation, in incorporation of other known channel effects, such as dispersion in time and frequency, will likely enable increased reliability of the system.

The present invention may be embodied on various computing platforms that perform actions responsive to software-based instructions. The following provides an antecedent basis for the information technology that may be utilized to enable the invention.

A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++ or the like and conventional procedural programming languages, such as the "C" programming language or similar programming languages.

Aspects of the present invention are described below with reference to illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between

What is claimed is:

1. A method for preventing unauthorized wireless communication with an implantable medical device, the method comprising:
   receiving a pilot signal request at an implantable medical device over a wireless channel and transmitting a pilot signal from the implantable medical device over the wireless channel in response to receiving the pilot signal request;
   receiving the pilot signal at a wearable external device and estimating the wireless channel, at the wearable external device, using the received pilot signal;
   pre-equalizing one or more command signals based upon the estimation of the wireless channel by the wearable external device to generate one or more wearable external device pre-equalized command signals;
   transmitting the one or more wearable external device pre-equalized command signals from the wearable external device over the wireless channel;
   receiving the one or more wearable external device pre-equalized command signals from the wearable external device at the implantable medical device;
   controlling the implantable medical device using the one or more wearable external device pre-equalized command signals received at the implantable medical device;
   receiving the pilot signal at an adversary device and estimating the wireless channel, at the adversary device, using the received pilot signal, wherein the estimation of the wireless channel using the received pilot signal at the adversary device is more erroneous than the estimation of the wireless channel using the received pilot signal at the wearable external device,
   pre-equalizing one or more command signals based upon the estimation of the wireless channel by the adversary device to generate one or more adversary device pre-equalized command signals;
   transmitting the one or more adversary device pre-equalized command signals from the adversary device over the wireless channel;
   receiving the one or more adversary device pre-equalized command signals from the adversary device at the implantable medical device; and
   failing to control the implantable medical device using the one or more adversary device pre-equalized command signals received at the implantable medical device as a result of the more erroneous estimation of the wireless channel by the adversary device.

2. The method of claim 1, further comprising, transmitting the pilot signal request from the wearable external device over the wireless channel.

3. The method of claim 1, further comprising:
   transmitting the pilot signal request from the adversary device over the wireless channel;
   receiving the pilot signal at the wearable external device and determining at the wearable external device that the wearable external device did not transmit the pilot signal request; and
   transmitting a jamming signal over the wireless channel to prevent the implantable medical device from receiving any signals transmitted from the adversary device over the wireless channel.

4. The method of claim 3, further comprising, applying a blocking mechanism at the implantable medical device to prevent the implantable medical device from receiving any signals transmitted over the wireless channel that exceed a predetermined signal power threshold.

5. The method of claim 4, where a power level of the jamming signal does not exceed the predetermined signal power threshold of the blocking mechanism.

6. The method of claim 3, wherein a distance between the adversary device and the implantable medical device is greater than a distance between the wearable external device and the implantable medical device.

7. The method of claim 1, wherein the implantable medical device is selected from the group consisting of pacemakers, implantable cardiac defibrillators (ICDs), drug delivery systems and neurostimulators.

8. A method for preventing unauthorized wireless communication with an implantable medical device, the method comprising:
   receiving a pilot signal request at an implantable medical device over a wireless channel and transmitting a pilot signal from the implantable medical device over the wireless channel in response to receiving the pilot signal request;
   receiving the pilot signal at the wearable external device;
   determining at the wearable external device if the wearable external device transmitted the pilot signal request received at the implantable device;
   if the wearable external device did not transmit the pilot signal request, transmitting a jamming signal over the wireless channel to prevent the implantable medical device from receiving any signals transmitted from an adversary device over the wireless channel; and
   if the wearable external device did transmit the pilot signal request, estimating the wireless channel, at the wearable external device, using the received pilot signal, pre-equalizing one or more command signals based upon the estimation of the wireless channel to generate one or more pre-equalized command signals, transmitting the pre-equalized command signals from the wearable external device over the wireless channel and receiving the pre-equalized command signals at the implantable medical device.

9. The method of claim 8, further comprising, applying a blocking mechanism at the implantable medical device to prevent the implantable medical device from receiving any signals transmitted over the wireless channel that exceed a predetermined signal power threshold.

10. The method of claim 9, where a power level of the jamming signal does not exceed the predetermined signal power threshold of the blocking mechanism.

11. The method of claim 8, wherein a distance between the adversary device and the implantable medical device is greater than a distance between the wearable external device and the implantable medical device.

12. The method of claim 8, wherein the implantable medical device is selected from the group consisting of pacemakers, implantable cardiac defibrillators (ICDs), drug delivery systems and neurostimulators.

13. A system comprising:
   an implantable medical device comprising circuitry for receiving a pilot signal request from an adversary device over a wireless channel and for transmitting a pilot signal over the wireless channel in response to receiving the pilot signal request; and
   a wearable external device comprising circuitry for receiving the pilot signal, for estimating the wireless channel using the received pilot signal, for pre-equalizing one or more command signals based upon the estimation of the wireless channel to generate one or more pre-equalized command signals, and for transmitting the pre-equalized command signals from the wearable external device over the wireless channel and circuitry for receiving the pilot signal, for determining that the wearable external device did not transmit the pilot signal request and for transmitting a jamming signal over the wireless channel to prevent the implantable medical device from receiving any signals transmitted from the adversary device over the wireless channel.

14. The system of claim 13, wherein the wearable external device further comprising circuitry for transmitting the pilot signal request from the wearable external device over the wireless channel.

15. The system of claim 13, wherein the implantable medical device further comprises circuitry for applying a blocking mechanism to prevent the implantable medical device from receiving any signals transmitted over the wireless channel that exceed a predetermined signal power threshold.

16. The system of claim 13, where a power level of the jamming signal does not exceed the predetermined signal power threshold.

17. The system of claim 13, wherein a distance between the adversary device and the implantable medical device is greater than a distance between the wearable external device and the implantable medical device.

18. The system of claim 13, wherein the implantable medical device is selected from the group consisting of pacemakers, implantable cardiac defibrillators (ICDs), drug delivery systems and neurostimulators.

* * * * *